United States Patent

Stroech et al.

[11] Patent Number: 5,096,913
[45] Date of Patent: Mar. 17, 1992

[54] SUBSTITUTED BIS-AZOLYL DERIVATIVES FOR COMBATING FUNGI IN PLANT PROTECTION

[75] Inventors: Klaus Stroech, Solingen; Susanne Backens-Hammerschmidt, Bergisch-Gladbach; Gerd Hänssler, Leverkusen; Stefan Dutzmann, Düsseldorf, all of Fed. Rep. of Germany

[73] Assignee: Bayer Aktiengesellschaft, Leverkusen, Fed. Rep. of Germany

[21] Appl. No.: 535,797

[22] Filed: Jun. 8, 1990

[30] Foreign Application Priority Data

Jun. 28, 1989 [DE] Fed. Rep. of Germany ....... 3921162

[51] Int. Cl.$^5$ .......................................... A01N 43/653
[52] U.S. Cl. ..................... 514/383; 514/184
[58] Field of Search ................... 514/383, 184

[56] References Cited

U.S. PATENT DOCUMENTS

| | | | |
|---|---|---|---|
| 4,870,088 | 9/1989 | Blume et al. | 514/340 |
| 4,875,928 | 10/1989 | Regel et al. | 514/184 |
| 4,910,213 | 3/1990 | Regel et al. | 514/383 |
| 4,960,781 | 10/1990 | Holmwood et al. | 514/383 |

*Primary Examiner*—Allen J. Robinson
*Assistant Examiner*—John D. Pak
*Attorney, Agent, or Firm*—Sprung Horn Kramer & Woods

[57] ABSTRACT

Combating phytopathogenic fungi with substituted bis-azolyl derivatives of the formula

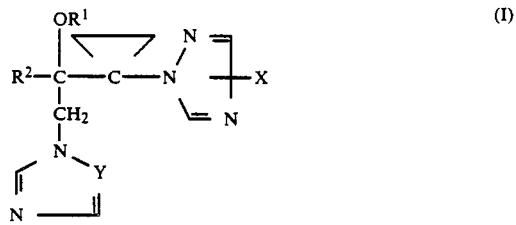

in which
- $R^1$ is hydrogen, optionally substituted alkyl, alkenyl, trialkylsilyl or alkylcarbonyl,
- $R^2$ is optionally substituted aryl or heterocyclic,
- X is halogen, and
- Y is a nitrogen atom or a CH group, and addition products thereof with acids and metal salts.

7 Claims, No Drawings

SUBSTITUTED BIS-AZOLYL DERIVATIVES FOR COMBATING FUNGI IN PLANT PROTECTION

The present invention relates to the use of substituted bis-azolyl derivatives for combating phytopathogenic fungi.

It has already been disclosed that certain bisazolyl derivatives are suitable as fungicides in plant protection (cf. U.S. Pat. No. 4,875,928).

For example, 1-(4-chlorophenyl)-1-[1-(1,2,4-triazol-1-yl)-cyclopropyl]-2-(1,2,4-triazol-1-yl)-1-ethanol and 1-(4-methylphenyl)-1-[1-(1,2,4-triazol-1-yl)-cyclopropyl]-2-(1,2,4-triazol-1-yl)-1-ethanol can be employed in plant protection for combating fungi. The action of these substances is good; in some cases, however, it leaves something to be desired when low application rates are used.

It has now been found that the substituted bisazolyl derivatives of the formula

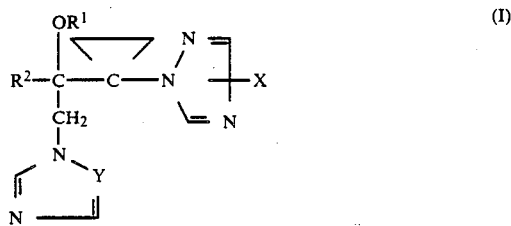

in which
R$^1$ represents hydrogen, or
represents straight-chain or branched alkyl which has up to 8 carbon atoms and is optionally substitued by aryl which, in turn, is optionally substituted by halogen, C$_1$–C$_8$-alkyl, C$_1$–C$_8$-alkoxy, C$_1$–C$_8$-alkylthio, C$_1$–C$_8$-halogenoalkyl, C$_1$–C$_8$-halogenoalkoxy, C$_1$–C$_8$-halogenoalkylthio or by phenyl which is optionally up to tetrasubstituted by identical or different halogen substituents, or
represents straight-chain or branched alkenyl or alkinyl, each of which has up to 8 carbon atoms, or
represents trialkylsilyl having up to 8 carbon atoms in the alkyl moiety, or
represents alkylcarbonyl having up to 8 carbon atoms in the alkyl moiety,
R$^2$ represents aryl which has 6 to 10 carbon atoms and which is optionally up to tetrasubstituted by identical or different substituents from the series comprising halogen, C$_1$–C$_8$-alkyl, C$_1$–C$_8$-alkoxy, C$_1$–C$_8$-alkylthio, halogenoalkyl having 1 to 8 carbon atoms and 1 to 5 identical or different halogen atoms, halogenoalkoxy having 1 to 8 carbon atoms and 1 to 5 identical or different halogen atoms, halogenoalkylthio having 1 to 8 carbon atoms and 1 to 5 identical or different halogen atoms, phenyl which is optionally monosubstituted to trisubstituted by halogen, phenoxy which is optionally monosubstituted to trisubstituted by halogen, and/or phenylthio which is optionally monosubstituted to trisubstituted by halogen, or
R$^2$ represents a 5- or 6-membered heterocyclic ring which can contain one or more hetero atoms, such as sulphur, oxygen or nitrogen, and which is optionally substituted by halogen, C$_1$–C$_8$-alkyl, C$_1$–C$_8$-alkoxy, C$_1$–C$_8$-alkylthio, halogenoalkyl having 1 to 8 carbon atoms and 1 to 5 identical or different halogen atoms, halogenoalkoxy having 1 to 8 carbon atoms and 1 to 5 identical or different halogen atoms, and/or halogenoalkylthio having 1 to 8 carbon atoms and 1 to 5 identical or different halogen atoms,
X represents halogen, and
Y represents a nitrogen atom or the CH group,
as well as their acid addition salts and metal salt complexes are highly suitable for combating fungi in plant protection.

The substances which can be used according to the invention contain one asymmetrically substituted carbon atom. They can therefore be obtained in the forms of optical isomers. The present invention relates to the use of the individual isomers and to their mixtures.

Surprisingly, the substances which can be used according to the invention have a considerably better activity for combating phytopathogenic fungi than 1-(4-chloro-phenyl)-1-[1-(1,2,4-triazol-1-yl)-cyclopropyl]-2-(1,2,4-triazol-1-yl)-1-ethanol and 1-(4-methylphenyl)-1-[1-(1,2,4-triazol-1-yl)-cyclopropyl]-2-(1,2,4-triazol-1-yl)-1-ethanol which are previously known active compounds of a similar chemical structure and the same direction of action.

The compounds of formula I are disclosed as antimycotics in U.S. application Ser. No. 422,827, filed Oct. 17, 1989, now pending.

Formula (I) provides a general definition of the substances which can be used according to the invention. Substances of the formula (I) which can preferably be used are those of the formula (I) in which
R$^1$ represents hydrogen, or
represents straight-chain or branched alkyl which has up to 6 carbon atoms and which is optionally substituted by phenyl which, in turn, can be substituted by halogen, C$_1$–C$_6$-alkyl, C$_1$–C$_6$-alkoxy, C$_1$–C$_6$-alkylthio, C$_1$–C$_6$-halogenoalkyl or by phenyl which is optionally up to trisubstituted by identical or different halogen substituents, or
represents straight-chain or branched alkenyl or alkinyl having up to 6 carbon atoms, or
represents trialkylsilyl having up to 6 carbon atoms in each alkyl moiety, or
represents alkylcarbonyl having up to 6 carbon atoms in the alkyl moiety,
R$^2$ represents phenyl or naphthyl, it being possible for each of these radicals to be monosubstituted to trisubstituted by identical or different substituents from the series comprising halogen, C$_1$–C$_6$-alkoxy, C$_1$–C$_6$-alkylthio, halogenoalkyl having 1 to 6 carbon atoms and 1 to 5 identical or different halogen atoms, halogenoalkoxy having 1 to 6 carbon atoms and 1 to 5 identical or different halogen atoms, halogenoalkylthio having 1 to 6 carbon atoms and 1 to 5 identical or different halogen atoms, phenyl which is optionally monosubstituted or disubstituted by fluorine, chlorine and/or bromine, phenoxy which is optionally monosubstituted or disubstituted by fluorine, chlorine and/or bromine, and/or by phenylthio which is optionally monosubstituted or disubstituted by fluorine, chlorine and/or bromine, or
R$^2$ represents a 5- or 6-membered heterocyclic ring having 1 to 3 oxygen, sulphur and/or nitrogen atoms, it being possible for each of these heterocyclic rings to be monosubstituted or disubstituted by identical or different substituents from the series comprising halogen, $C_1$–$C_6$-alkyl, $C_1$–$C_6$-alkoxy, $C_1$–$C_6$-alkylthio, halogenoalkyl having 1 to 6 carbon atoms and 1 to 5 identical or different halogen atoms, halogenoalkoxy having 1 to 6 carbon atoms and 1 to 5 identical or different halogen atoms, and/or by halogenoalkylthio having 1 to 6 carbon atoms and 1 to 5 identical or different halogen atoms, X represents halogen, and Y represents a nitrogen atom or the CH group.

Substances which can particularly preferably be used are those of the formula (I) in which $R^1$ represents hydrogen, or
  represents straight-chain or branched alkyl which has up to 4 carbon atoms and is optionally substituted by phenyl which, in turn, is substituted by fluorine, chlorine, bromine, methyl, methoxy, methylthio, trifluoromethyl and/or by phenyl which is optionally monosubstituted or disubstituted by fluorine, chlorine and/or bromine, or
  represents straight-chain or branched alkenyl or alkinyl, each of which has up to 4 carbon atoms,
  represents trimethylsilyl or alkylcarbonyl having 1 to 4 carbon atoms in the alkyl moiety, $R^2$ represents phenyl or naphthyl, it being possible for each of these radicals to be monosubstituted or disubstituted by identical or different substituents from the series comprising fluorine, chlorine, bromine, methyl, ethyl, n-propyl, isopropyl, n-butyl, tert.-butyl, methoxy, ethoxy, methylthio, ethylthio, trifluoromethyl, trifluoromethoxy, trifluoromethylthio, phenyl, phenoxy, chlorophenyl, chlorophenoxy, fluorophenyl and/or fluorophenoxy, or $R^2$ represents a 5- or 6-membered heterocyclic ring having 1 to 3 oxygen, sulphur and/or nitrogen atoms, it being possible for each of these heterocyclic rings to be monosubstituted or disubstituted by identical or different substituents from the series comprising fluorine, chlorine, bromine, methyl, ethyl, methoxy, ethoxy, methylthio, trifluoromethyl, trifluoromethoxy and/or by trifluoromethylthio, X represents fluorine, chlorine or bromine and Y represents a nitrogen atom or the CH group.

Other compounds according to the invention which can preferably be used are addition products of acids and those substituted bis-azolyl derivatives of the formula (I) in which $R^1$, $R^2$, X and Y have the meanings which have already been mentioned as being preferred for these radicals.

The acids which can be added on preferably include hydrohalic acids, such as, for example, hydrochloric acid and hydrobromic acid, in particular hydrochloric acid, furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, as well as sulphonic acids, such as, for example, p-toluenesulphonic acid, 1,5-naphthalenedisulphonic acid or camphorsulphonic acid.

Other compounds according to the invention which can preferably be used are addition products of salts of metals of main groups II to IV and of subgroups I and II as well as IV to VIII of the Periodic System of the Elements and those substituted bis-azolyl derivatives of the formula (I) in which $R^1$, $R^2$, X and Y have the meanings which have already been mentioned as being preferred for these radicals.

Amongst these, the salts of copper, zinc, manganese, magnesium, tin, iron and of nickel are particularly preferred. Suitable anions of these salts are those which are derived from those acids which lead to physiologically acceptable addition products.

Particularly preferred acids of this type in this connection are the hydrohalic acids, such as, for example, hydrochloric acid and hydrobromic acid, and furthermore phosphoric acid, nitric acid and sulphuric acid.

The substances which can be used according to the invention are the subject-matter of a separate patent application. They can be prepared by a process in which a) azolyl-cyclopropyl ketones of the formula

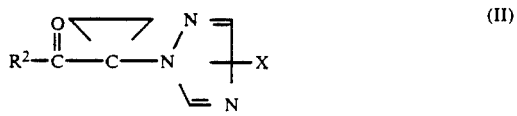

in which $R^2$ and X are as defined above, are reacted in a first step either

α) with dimethyloxosulphonium methylide, of the formula

or

β) with dimethylsulphonium methylide, of the formula

in the presence of a diluent, and the resulting azolylcyclopropyl-oxiranes of the formula

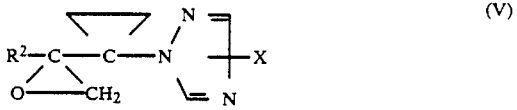

in which $R^2$ and X are as defined above, are reacted, in a second step, with azoles of the formula

in which

Y is as defined above, in the presence of a diluent and in the presence of a base, or b) bis-azolyl-keto derivatives of the formula

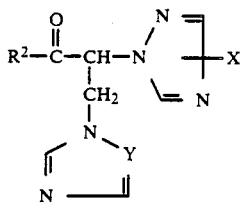

in which
R², X and Y are as defined above,
are reacted with dimethyloxosulphonium methylide, of the formula

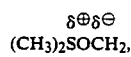

in the presence of a diluent, or
c) hydroxy compounds of the formula

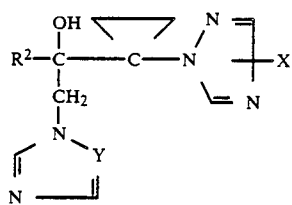

in which
R², X and Y are as defined above,
are reacted with bases in the presence of a diluent and the resulting alcoholates of the formula

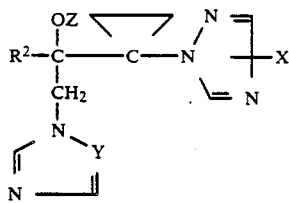

in which
R², X and Y are as defined above and
Z represents a radical derived from the cationic part of a base, are reacted with halogen compounds of the formula

 (VIII)

in which
R³ represents straight-chain or branched alkyl which has up to 8 carbon atoms and which is optionally substituted by aryl which, in turn, is substituted by halogen, $C_1$-$C_8$-alkyl, $C_1$-$C_8$-alkoxy, $C_1$-$C_8$-alkylthio, $C_1$-$C_8$-halogenoalkyl, $C_1$-$C_8$-halogenoalkoxy, $C_1$-$C_8$-halogenoalkylthio or by phenyl which is optionally up to tetrasubstituted by identical or different halogen substituents, or
represents straight-chain or branched alkenyl or alkinyl, each of which has up to 8 carbon atoms, or
represents trialkylsilyl having up to 8 carbon atoms in the alkyl moiety, or represents alkylcarbonyl having up to 8 carbon atoms in the alkyl moiety, and
Hal represents chlorine, bromine or iodine, in the presence of a diluent;
and, if appropriate, the resulting compounds of the formula (I) are subsequently subjected to an addition reaction with an acid or a metal salt.

The azolyl-cyclopropyl ketones of the formula (II) required as starting substances in process a) may be prepared by reacting halogeno-propyl ketones of the formula

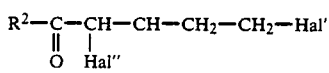

in which
R² is as defined above and
Hal' and Hal" are identical or different and represent chlorine or bromine,
with triazoles of the formula

in which
X is as defined above,
in the presence of a diluent and in the presence of a base.

Suitable diluents for the preparation of the ketones of the formula (II) are organic solvents which are inert under the reaction conditions. These preferably include alcohols, such as, for example, ethanol, methoxyethanol or propanol, ketones, such as, for example, acetone and 2-butanone, nitriles, such as, for example, acetonitrile, esters, such as, for example, ethyl acetate, ethers, such as, for example, dioxane, aromatic hydrocarbons, such as, for example, benzene and toluene, or amides, such as, for example, dimethylformamide.

Bases which are possible for this reaction are all inorganic or organic bases which can customarily be used. These preferably include alkali metal carbonates, such as, for example, sodium carbonate and potassium carbonate, alkali metal hydroxides, such as, for example, sodium hydroxide, alkali metal alcoholates, such as, for example, sodium methylate, sodium ethylate, potassium methylate and potassium ethylate, alkali metal hydrides, such as, for example, sodium hydroxide, and also lower tertiary alkylamines, cycloalkylamines and aralkylamines, such as, in particular, triethylamine.

When carrying out this reaction, the reaction temperatures can be varied within a substantial range. In general, the process is carried out at temperatures of between 0° C. and 200° C., preferably between 60° C. and 150° C.

When this reaction is carried out, 1 to 2 moles of triazole of the formula (X) and, if appropriate, 1 to 2 moles of base are generally employed per mole of halogeno-propyl ketone of the formula (IX). The azolylcyclopropyl ketones of the formula (II) are isolated by customary methods.

The halogeno-propyl ketones of the formula (IX) are known or may be prepared in a simple manner by customary methods (cf. DE-OS (German Published Specification) 2,521,104, DE-OS (German Published Specification) 2,320,355 and DE-OS (German Published Specification) 2,351,948).

Dimethyloxosulphonium methylide, of the formula (III), which is required as a reactant in process (a, variant α), as well as in process (b), is known (cf. J. Am. Chem. Soc. 87, 1363-1364 (1965)). In the above reactions it is processed in the freshly prepared state, by preparing it in situ by reacting trimethyloxosulphonium iodide with sodium hydride or sodium amide, in particular with potassium tert.-butylate or sodium methylate, in the presence of a diluent.

Dimethylsulphonium methylide, of the formula (IV), which is required as a reactant in process (a, variant β), is likewise known (cf. Heterocycles 8, (1977) 397). It is likewise used in the freshly prepared state in the above reaction.

The azoles of the formula (VI) which are required as starting substances in the second step of process (a) are generally known compounds of organic chemistry.

The bis-azolyl-keto derivatives of the formula (VII) which are required as starting substances in process (b) may be prepared by reacting azolyl ketones of the formula

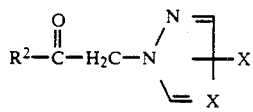

(XI)

in which
R$^2$ and X are as defined above,
with hydroxymethylazoles of the formula

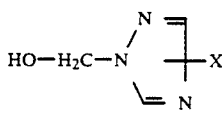

(XII)

in which
Y is as defined above,
in the presence of a catalyst and in the presence of a diluent.

Suitable diluents for this process for the preparation of the bis-azolyl-keto derivatives of the formula (VII) are preferably inert organic solvents. These preferably include alcohols, such as methanol and ethanol, ethers, such as tetrahydrofuran and dioxane, aromatic hydrocarbons, such as benzene and toluene, and also halogenated aliphatic and aromatic hydrocarbons, such as methylene chloride, chloroform, chlorobenzene and dichlorobenzene.

This process is carried out in the presence of a catalyst. All acid and, in particular, basic catalysts which can customarily be used, as well as their mixtures with buffers, can be employed. They preferably include Lewis acids, such as, for example, boron trifluoride, boron trichloride, tin tetrachloride or titanium tetrachloride, organic bases, such as pyridine and piperidine, and, in particular, piperidine acetate.

When this process is carried out, the reaction temperatures can be varied within a substantial range. In general, it is carried out at between 20° and 160° C., preferably at the boiling point of the specific solvent.

When the process for the preparation of the bisazolyl-keto derivatives of the formula (VII) is carried out, 1 to 1.5 moles of hydroxymethylazole of the formula (XII) and catalytic to 0.2 molar amounts of catalyst are employed per mole of azolyl ketone of the formula (XI).

The azolyl ketones of the formula (XI) are known (cf. DE-OS (German Published Specification) 2,431,407, DE-OS (German Published Specification) 2,610,022 and DEOS (German Published Specification) 2,638,470).

The hydroxymethylazoles of the formula (XII) are likewise known (cf. EP-OS (European Published Specification) 0,006,102, and Chem. Heterocycl. Comp. 1980, 189).

The hydroxy compounds of the formula (Ia) to be used as starting substances for process (c) are compounds which can be used according to the invention. They are converted into alcoholates of the formula (Ib) with the aid of strong bases. Bases which can preferably be used for this purpose are alkali metal amides, such as sodium amide and potassium amide, furthermore alkali metal hydrides, such as sodium hydride, and quaternary ammonium hydroxides and phosphonium hydroxides. Z in the compounds of the formula (Ib) therefore preferably represents sodium, potassium, quaternary ammonium or phosphonium.

Possible diluents for the reaction of the compounds of the formula (Ia) to give the alcoholates of the formula (Ib) are inert organic solvents. Ethers, such as dioxane, can preferably be used.

The reaction of the compounds of the formula (Ia) to give the alcoholates of the formula (Ib) preferably takes place at room temperature.

Formula (VIII) provides a general definition of the halogen compounds which are required as reactants in process (c). In this formula, R$^3$ preferably represents those meanings which have already been mentioned as being preferred for the substituent R$^1$ in connection with the description of the substances of the formula (I) which can be used according to the invention, with the exception of the meaning of hydrogen. Hal represents chlorine, bromine or iodine.

The halogen compounds of the formula (VIII) are generally known compounds of organic chemistry.

Possible diluents for the first step of process (a) are inert organic solvents. These preferably include ethers, such as tetrahydrofuran or dioxane, aliphatic and aromatic hydrocarbons, such as, in particular, benzene, toluene or xylene, and also dimethyl sulphoxide.

When the first step of process (a) is carried out, the reaction temperatures can be varied within a substantial range. In general, the process is carried out at between 0° and 100° C., preferably between 10° and 60° C.

When the first step of process (a) is carried out, 1 to 3 moles of dimethyloxosulphonium methylide of the formula (III), prepared in situ from trimethyloxosulphonium iodide in dimethyl sulphoxide and sodium hydride, or of dimethylsulphonium methylide of the formula (V) are preferably employed per mole of azolylcyclopropyl ketone of the formula (II).

The intermediates of the formula (V) are isolated in a generally customary manner.

Possible diluents for the second step of process (a) are inert organic solvents. Nitriles, such as, in particular, acetonitrile, aromatic hydrocarbons, such as benzene, toluene and dichlorobenzene, formamides, such as, in particular, dimethylformamide, and also hexamethylphosphoric triamide, can preferably be used.

The second step of process (a) is carried out in the presence of a base. Possible bases for this purpose are all inorganic and organic bases which can customarily be used. These preferably include alkali metal carbonates, such as, for example, sodium carbonate and potassium carbonate, alkali metal hydroxides, such as, for example, sodium hydroxide, alkali metal alcoholates, such as, for example, sodium methylate, sodium ethylate, potassium methylate and potassium ethylate, alkali metal hydrides, such as, for example, sodium hydride, and also lower tertiary alkylamines, cycloalkylamines and aralkylamines, such as, in particular, triethylamine.

When the second step of process (a) is carried out, the reaction temperatures can be varied within a substantial range. In general, the process is carried out at temperatures of between 0° C. and 200° C., preferably between 60° C. and 150° C.

When the second step of process (a) is carried out, 1 mole of oxirane of the formula (V), 1 to 2 moles of azole of the formula (VI) and 1 to 2 moles of base are preferably employed. The end products are isolated in a generally customary manner.

The reaction conditions for carrying out process (b) correspond to those for carrying out the first step of process (a).

Possible diluents in the reaction of alcoholates of the formula (Ib) with halogen compounds of the formula (VIII) in process (c) are inert organic solvents. These preferably include ethers, such as diethyl ether or dioxane, aromatic hydrocarbons, such as benzene, in individual cases also chlorinated hydrocarbons, such as chloroform, methylene chloride or carbon tetrachloride, and also hexamethylphosphoric acid triamide.

When the alcoholates of the formula (Ib) are reacted with halogen compounds of the formula (VIII) in process (c), the reaction temperatures can be varied within a substantial range. In general, the process is carried out at temperatures of between 0° C. and 120° C., preferably between 20° C. and 100° C.

When process (c) is carried out, 1 to 2 moles of a halogen compound of the formula (VIII) are preferably employed per mole of an alcoholate of the formula (Ib). To isolate the end product, the reaction mixture is freed from the solvent, and water and an organic solvent are added to the residue. The organic phase is separated and worked up and purified in a customary manner.

In a preferred embodiment in process (c), a procedure is advantageously followed in which, starting from a hydroxyl compound of the formula (Ia), the latter, in a suitable organic solvent, is converted by means of an alkali metal hydride or alkali metal amide into an alkali metal alcoholate of the formula (Ib), and the latter is reacted immediately, without isolation, with a halogen compound of the formula (VIII), by which procedure the compounds of the formula (I) according to the invention are obtained in one step, with alkali metal halide being eliminated.

Following a further preferred embodiment of process (c), the alcoholates of the formula (Ib) and the reaction with compounds of the formula (VIII) are advantageously carried out in a two-phase system, such as, for example, aqueous sodium hydroxide or potassium hydroxide solution/toluene or methylene chloride, with the addition of 0.01 to 1 mole of a phase transfer catalyst, such as, for example, an ammonium or phosphonium compound, the alcoholates and the halogen compounds present in the organic phase being reacted in the organic phase or at the interface.

The bis-azolyl derivatives of the formula (I) can be converted into acid addition salts or metal salt complexes.

Possible acids for the preparation of acid addition salts of the compounds of the formula (I) are preferably those which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert organic solvent and adding the acid, for example hydrochloric acid, and they can be isolated in a known manner, for example by filtration, and, if appropriate, purified by washing with an inert organic solvent.

Possible salts for the preparation of metal salt complexes of the compounds of the formula (I) are preferably those salts of metals which have already been mentioned as being preferred metal salts in connection with the description of the metal salt complexes according to the invention.

The metal salt complexes of the compounds of the formula (I) can be obtained in a simple manner by customary methods, for example by dissolving the metal salt in alcohol, for example ethanol, and adding the solution to compounds of the formula (I). Metal salt complexes can be isolated in a known manner, for example by filtration, and, if appropriate, they can be purified by recrystallization.

The active compounds according to the invention have a powerful microbicidal action and can be employed as fungicides in plant protection and in the protection of materials.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae;*

Pseudomonas species, such as *Pseudomonas lachrymans;*

Erwinia species, such as *Erwinia amylovora;*

Pythium species, such as *Pythium ultimum;*

Phytophthora species, such as *Phytophthora infestans;*

Pseudoperonospora species such as *Pseudoperonospora humuli* or *Pseudoperonospora cubense;*

Plasmopara species, such as *Plasmopara viticola;*

Peronospora species, such as *Peronospora pisi* or *P. brassicae;*

Erysiphe species, such as *Erysiphe graminis;*

Sphaerotheca species, such as *Sphaerotheca fuliginea;*

Podosphaera species, such as *Podosphaera leucotricha;*

Venturia species, such as *Venturia inaequalis;*

Pyrenophora species, such as *Pyrenophora teres* or *P. graminea;* (conidia form: Drechslera, syn: Helminthosporium);

Cochliobolus species, such as *Cochliobolus sativus;* (conidia form: Drechslera, syn: Helminthosporium);

Uromyces species, such as *Uromyces appendiculatus;*

Puccinia species, such as *Puccinia recondita;*

Tilletia species, such as *Tilletia caries;*

Ustilago species, such as *Ustilago nuda* or *Ustilago avenae;*

Pellicularia species, such as *Pellicularia sasakii;*

Pyricularia species, such as *Pyricularia oryzae;*

Fusarium species, such as *Fusarium culmorum;*

Botrytis species, such as *Botrytis cinerea;*

Septoria species, such as *Septoria nodorum;*

Leptosphaeria species, such as *Leptosphaeria nodorum;*

Cercospora species, such as *Cercospora canescens;*

Alternaria species, such as *Alternaria brassicae* and

Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The compounds according to the invention are particularly suitable for combating diseases of cereals and rice. For example, diseases which can be combated particularly effectively are mildew diseases and rust diseases, *Puccinia recondita, Pyrenophora teres, Cochliobolus sativus, Erysiphe graminis* and *Septoria nodorum* on cereals as well as Pyricularia and Pellicularia on rice.

Furthermore, they can be used very successfully against *Sphaerotheca fuliginea* on cucumbers, *Venturia inaequalis* on apples, *Uromyces appendiculatus* on beans and *Cercospora canescens* on beans.

The substances which can be used according to the invention are furthermore also distinguished by herbicidal and plant growth regulating properties.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, and furthermore natural phospholipids, such as cephalins and lecithins, and synthetic phospholipids. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds which can be used according to the invention can be present in the formulations as a mixture with other known active compounds, such as fungicides, insecticides, acaricides and herbicides, as well as mixtures with fertilizers and other growth regulators.

The active compounds can be used as such or in the form of their formulations or the use forms prepared therefrom by further dilution, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like.

It is furthermore possible to apply the active compounds by the ultra-low volume method or to inject the active compound preparation or the active compound itself into the soil. The seeds of the plants can also be treated.

When the substances which can be used according to the invention are employed as fungicides, the application rate can be varied within a substantial range, depending on the type of application. For example, the concentrations of active compound in the treatment of parts of plants in the use forms are generally between 1 and 0.0001% by weight, preferably between 0.5 and 0.001%. In the treatment of seeds, amounts of active compound of 0.001 to 50 g per kilogram of seed, preferably 0.01 to 10 g, are generally required. In the treatment of the soil, concentrations of active compound of 0.00001 to 0.1% by weight, preferably of 0.0001 to 0.02%, are required at the site of action.

When the compounds which can be used according to the invention are employed as plant growth regulators, the applications can be varied within a substantial range. In general, 0.01 to 50 kg, preferably 0.05 to 10 kg, of active compound are used per hectare of soil area.

For application of the substances which can be used according to the invention as plant growth regulators, they are used within a preferred period of time whose exact limitation depends on the climatic and vegetative circumstances.

The preparation and the use of the active compounds which can be used according to the invention can be seen from the examples which follow.

Preparation Examples

EXAMPLE 1

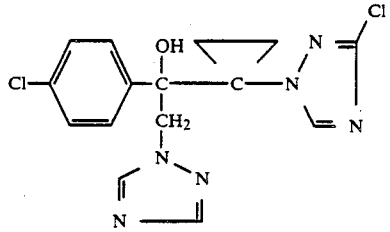

A solution of 21 g (0.071 mol) of 2-(4-chlorophenyl)-2-[1-(3-chloro-1,2,4-triazol-1-yl)-cyclopropyl]-oxirane in 30 ml of absolute dimethylformamide is added dropwise at 80° C. to a stirred mixture of 15.6 g (0.276 mol) of 1,2,4-triazole and 1.7 g (0.015 mol) of potassium tert.-butylate in 40 ml of absolute dimethylformamide. The reaction mixture is stirred for 6 more hours at 100° C. and then concentrated by stripping off the solvent under reduced pressure. The residue which remains is taken up in a mixture of ethyl acetate/toluene, and the mixture is washed with water, dried over sodium sulphate and concentrated under reduced pressure. The residue is chromatographed on silica gel using a mixture of dichloromethane/ethanol=98:2 as the eluent. Concentration of the eluate by evaporation gives 11.5 g of 1-(4-chlorophenyl)-1-[1-(3-chloro-1,2,4-triazol-1-yl)-cyclopropyl]-2-(1,2,4-triazol-1-yl)-ethan-1-ol in the form of a solid of melting point 156° C.

Preparation of the starting substances

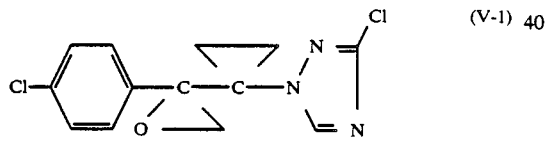

60 ml of absolute dimethyl sulphoxide are added dropwise at 10° C. under a nitrogen atmosphere to a stirred mixture of 2.5 g (83 mmol) of sodium hydride (80 per cent of substance) and 17.6 g (80 mmol) of trimethyl sulphoxonium iodide. Stirring is continued for one hour at 20° C., and a solution of 20 g (71 mmol) of 1-(4-chlorobenzoyl)-1-(3-chloro-1,2,4-triazol-1-yl)-cyclopropane in 30 ml of dimethyl sulphoxide is subsequently added at 10° C. After the reaction mixture has been stirred for 48 hours at 20° C., it is warmed for another hour at 40° C. and then poured into water. The mixture is extracted several times using ethyl acetate, and the combined organic phases are washed with water, dried over sodium sulphate and concentrated by stripping off the solvent under reduced pressure. This procedure gives 21 g (100% of theory) of 2-(4-chlorophenyl)-2-[1-(3-chloro-1,2,4-triazol-1-yl)-cyclopropyl]-oxirane in the form of an oil. $^{1}$H-NMR (200 MHz, CDCl$_3$): δ=0.8-1.4 (m, 4H); 2.92 (d, 1H); 3.15 (d, 1H); 7.10 (d, 2H); 7.38 (d, 2H); 7.75 (s, 1H).

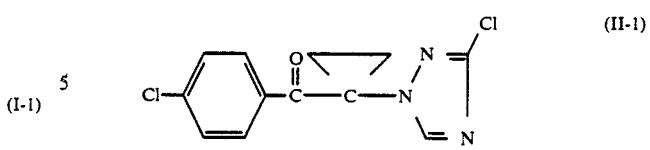

A mixture of 34 g (246 mmol) of potassium carbonate and 35 g (338 mmol) of 3-chloro-1,2,4-triazole in 130 ml of acetone is refluxed. To this mixture there is added dropwise a solution of 50 g (169 mmol) of 2-bromo-4-chloro-1-(4-chlorophenyl)-butan-1-one in 60 ml of acetone. The mixture is boiled under reflux for a further 8 hours, the solid residue is then filtered off with suction, and the solvent is stripped off under reduced pressure. The residue which remains is taken up in ethyl acetate. The solution is washed with water, dried over sodium sulphate and concentrated under reduced pressure. The residue which remains is chromatographed on silica gel using dichloromethane as the eluent. Concentration of the eluate by evaporation gives 42.9 g (90% of theory) of 1-(4-chlorobenzoyl)-1-(3-chloro-1,2,4-triazol-1-yl)-cyclopropane in the form of a solid of melting point 85° C.

EXAMPLE 2

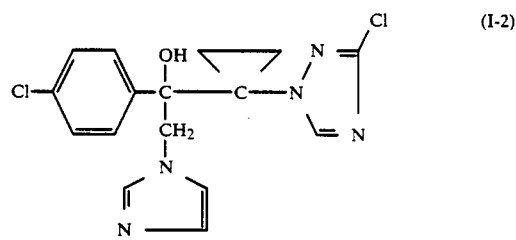

A mixture of 13 g (191 mmol) of imidazole and 1 g (9 mmol) of potassium tert.-butylate in 100 ml of acetonitrile is refluxed under a nitrogen atmosphere. To this mixture there is added dropwise a solution of 18 g (61 mmol) of 2-(4-chlorophenyl)-2-[1-(3-chloro-1,2,4-triazol-1-yl)-cyclopropyl]-oxirane in 30 ml of acetonitrile. The reaction mixture is refluxed for a further 10 hours and then concentrated by stripping off the solvent under reduced pressure. The residue which remains is taken up in ethyl acetate and washed with water. The organic phase is dried over sodium sulphate and then concentrated by stripping off the solvent under reduced pressure. The residue which remains is chromatographed on silica gel using a mixture of dichloromethane/ethanol=90:10 as the eluent. Concentration of the eluate gives 7.1 g (32% of theory) of 1-(4-chlorophenyl)-1-[1-(3-chloro-1,2,4-triazol-1-yl)-cyclopropyl]-2-(imidazol-1-yl)-ethan-1-ol in the form of a solid of melting point 231° C.

The substances listed in the examples which follow are also prepared following the previously mentioned methods.

EXAMPLE 3

1-[1-(3-Chloro-1,2,4-triazol-1-yl)-cyzlopropyl]-1-phenyl-2-(1,2,4-triazol-1-yl)-ethan-1-ol

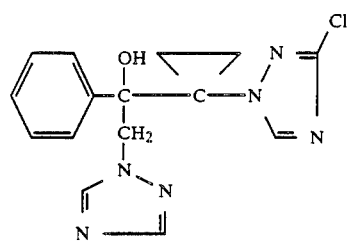
(I-3)

M.p.: 134° C.

EXAMPLE 4

1-[1-(3-Chloro-1,2,4-triazol-1-yl)-cyclopropyl -1-(4-fluoropheny)-2-(1,2,4-triazol-1-yl)-ethan-1-ol

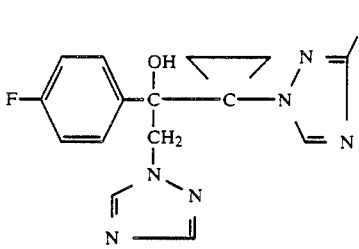
(I-4)

M.p.: 116° C.

EXAMPLE 5

1-[1-(3-Chloro-1,2,4-triazol-1-yl)-cyclopropyl]-1-(4-methylphenyl)-2-(1,2,4-triazol-1-yl)-ethan-1-ol

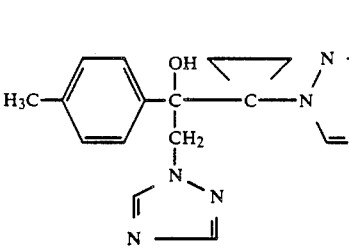
(I-5)

M.p.: 119° C.

EXAMPLE 6

1-(4-Biphenyl)-1-[1-(3-chloro-1,2,4-triazol-1-yl)-cyclopropyl]-2-(1,2,4-triazol-1-yl)-ethan-1-ol

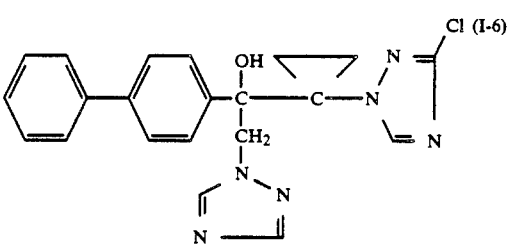
(I-6)

M.p: 150° C.

EXAMPLE 7

1-[1-(3-Chloro-1,2,4-triazol-1-yl)-cyclopropyl]-1-(2,4-difluorophenyl)-2-(1,2,4-triazol-1-yl)-ethan-1-ol

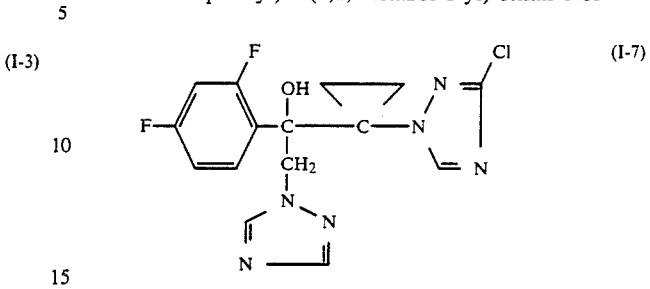
(I-7)

M.p.: 114° C.

EXAMPLE 8

1-[1-(3-Chloro-1,2,4-triazol-1-yl)-cyclopropyl]-1-(3,4-difluorophenyl)-2-(1,2,4-triazol-1-yl)-ethan-1-ol

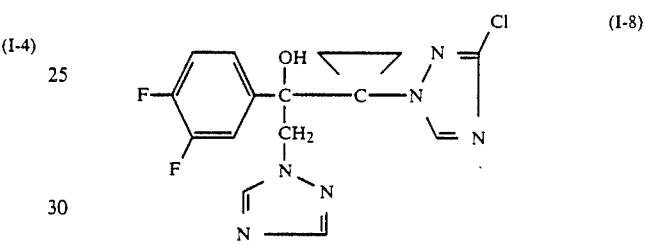
(I-8)

M.p.: 106° C.

EXAMPLE 9

1-(3-Chloro-1,2,4-triazol-1-yl)-1-(4-fluorobenzoyl)-cyclopropane

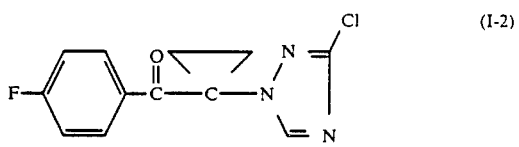
(I-2)

M.p.: 84° C.

USE EXAMPLES

Example A

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

The active compound, concentrations of active compound and test results can be seen from Table A below.

TABLE A

| Active compounds | Pyricularia test (rice)/protective | |
| --- | --- | --- |
| | Concentration of active compound in % | Degree of effectiveness in % of the untreated control |
| disclosed in EP-OS (European Published Specification) 0,180,838: | | |
| (A) [structure: 4-chlorophenyl-C(=O)-cyclopropyl-triazole] | 0.025 | 0 |
| (B) [structure: biphenyl-C(=O)-cyclopropyl-triazole] | 0.025 | 23 |
| (C) [structure: 4-bromophenyl-C(OH)(CH₂-triazole)-cyclopropyl-triazole] | 0.025 | 10 |
| according to the invention: | | |
| (I-1) [structure: 4-chlorophenyl-C(OH)(CH₂-triazole)-cyclopropyl-(chloro-triazole)] | 0.025 | 80 |
| (I-4) [structure: 4-fluorophenyl-C(OH)(CH₂-triazole)-cyclopropyl-(chloro-triazole)] | 0.025 | 86 |
| (I-3) [structure: phenyl-C(OH)(CH₂-triazole)-cyclopropyl-(chloro-triazole)] | 0.025 | 80 |

TABLE A-continued

Pyricularia test (rice)/protective

| Active compounds | Concentration of active compound in % | Degree of effectiveness in % of the untreated control |
| --- | --- | --- |
| (I-8) | 0.025 | 80 |
| (I-5) | 0.025 | 70 |
| (I-6) | 0.025 | 80 |

EXAMPLE B

Pyricularia test (rice)/systemic
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at 25° C. and a relative atmospheric humidity of 100% until they are evaluated.

Evaluation of the disease infestation is carried out 4 days after the inoculation.

The active compounds, concentrations of active compounds and tests results can be seen from Table B below.

TABLE B

Pyricularia test (rice)/systemic

| Active compound | Application rate in mg of active compound per 100 cm² | Degree of effectiveness in % of the untreated control |
| --- | --- | --- |
| disclosed in EP-OS (European Published Specification) 0,180,838: | | |
| (A) | 100 | 20 |
| (B) | 100 | 0 |

TABLE B-continued
Pyricularia test (rice)/systemic
| Active compound | Application rate in mg of active compound per 100 cm² | Degree of effectiveness in % of the untreated control |
|---|---|---|
| (C) 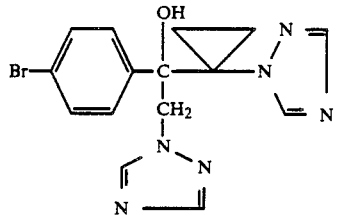 | 100 | 50 |
| according to the invention: | | |
| (I-1) 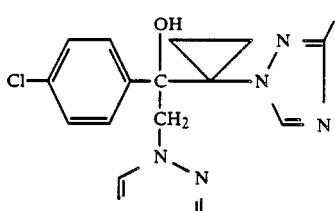 | 100 | 90 |
| (I-4) 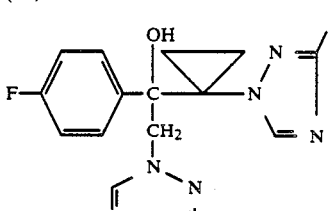 | 100 | 100 |
| (I-3) 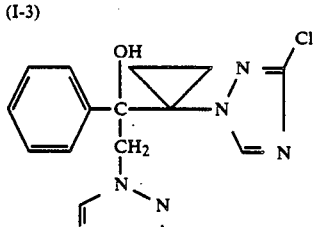 | 100 | 90 |
| (I-8) 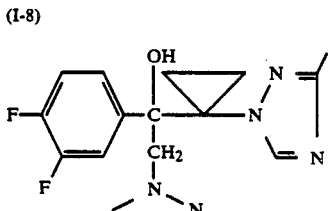 | 100 | 100 |

TABLE B-continued

| | Pyricularia test (rice)/systemic | |
|---|---|---|
| Active compound | Application rate in mg of active compound per 100 cm$^2$ | Degree of effectiveness in % of the untreated control |
| (I-5) | 100 | 100 |
| (I-6) | 100 | 100 |

EXAMPLE C

Cochliobolus sativus test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of Cochliobolus sativus. The plants remain in an incubation cabin for 48 hours at 20° C. and 100% relative atmospheric humidity.

The plants are placed in a greenhouse at a temperature of about 20° C. and a relative atmospheric humidity of about 80%.

Evaluation is carried out 7 days after inoculation.

The active compounds, concentrations of active compounds and tests results can be seen from Table C below.

TABLE C

| | Cochliobolus sativus test (barley)/protective | |
|---|---|---|
| Active compounds | Concentration of active compound in the spray liquor in % by weight | Degree of effectiveness in % of the untreated control |
| disclosed in EP-OS (European Published Specification) 0,180,838: | | |
| (D) | 0.025 | 0 |
| (E) | 0.025 | 11 |

TABLE C-continued

Cochliobolus sativus test (barley)/protective

| Active compounds | Concentration of active compound in the spray liquor in % by weight | Degree of effectiveness in % of the untreated control |
|---|---|---|
| (F) 4-methylphenyl derivative | 0.025 | 25 |
| (G) 2-chlorophenyl derivative | 0.025 | 0 |
| (H) 4-(4-chlorophenoxy)phenyl derivative | 0.025 | 0 |
| (J) 4-fluoro-2-chlorophenyl derivative | 0.025 | 0 |
| (K) 4-chlorophenyl derivative (imidazole) | 0.025 | 25 |
| (L) 2,4-difluorophenyl derivative (imidazole) | 0.025 | 0 | according to the invention:

TABLE C-continued

Cochliobolus sativus test (barley)/protective

| Active compounds | Concentration of active compound in the spray liquor in % by weight | Degree of effectiveness in % of the untreated control |
|---|---|---|
| (I-6) [biphenyl-substituted compound with OH, CH₂, cyclopropyl-triazole and chloro-triazole groups] | 0.025 | 81 |
| (I-4) [4-fluorophenyl-substituted compound with OH, CH₂, cyclopropyl-triazole and chloro-triazole groups] | 0.025 | 83 |

EXAMPLE D

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of mildew pustules.

Evaluation is carried out 7 days after the inoculation.

The active compounds, concentrations of active compound and test results can be seen from Table D below.

TABLE D

Erysiphe test (barley)/protective

| Active compounds | Concentration of active compound in the spray liquor in % by weight | Degree of effectiveness in % of the untreated control |
|---|---|---|
| disclosed in EP-OS (European Published Specification) 0,180,838: | | |
| (D) [4-methoxyphenyl-substituted compound with OH, CH₂, cyclopropyl-triazole and triazole groups] | 0.025 | 25 |
| (M) [4-chlorophenyl-substituted compound with OH, CH₂, cyclopropyl-triazole and triazole groups] | 0.025 | 25 |

TABLE D-continued

Erysiphe test (barley)/protective

| Active compounds | Concentration of active compound in the spray liquor in % by weight | Degree of effectiveness in % of the untreated control |
|---|---|---|
| (N) [biphenyl-C(OH)(CH₂-triazole)-cyclopropyl-triazole] | 0.025 | 34 | according to the invention

| | | | |
|---|---|---|---|
| (I-6) | [biphenyl-C(OH)(CH₂-triazole)-cyclopropyl-N=N-C(Cl)=N-CH] | 0.025 | 100 |
| (I-1) | [4-Cl-phenyl-C(OH)(CH₂-triazole)-cyclopropyl-N=N-C(Cl)=N-CH] | 0.025 | 100 |
| (I-4) | [4-F-phenyl-C(OH)(CH₂-triazole)-cyclopropyl-N=N-C(Cl)=N-CH] | 0.025 | 100 |
| (I-3) | [phenyl-C(OH)(CH₂-triazole)-cyclopropyl-N=N-C(Cl)=N-CH] | 0.025 | 88 |
| (I-7) | [2,4-F₂-phenyl-C(OH)(CH₂-triazole)-cyclopropyl-N=N-C(Cl)=N-CH] | 0.025 | 100 |

TABLE D-continued

| | Erysiphe test (barley)/protective | |
|---|---|---|
| Active compounds | Concentration of active compound in the spray liquor in % by weight | Degree of effectiveness in % of the untreated control |
| (I-8) | 0.025 | 88 |
| (I-5) | 0.025 | 100 |
| (I-2) | 0.025 | 75 |

It is understood that the specification and examples are illustrative but not limitative of the present invention and that other embodiments within the spirit and scope of the invention will suggest themselves to those skilled in the art.

We claim:

1. A method of combating phytopathogenic fungi which comprises applying to such fungi or to a locus from which it is desired to exclude such fungi a fungicidally effective amount of substituted bis-azolyl derivative of the formula

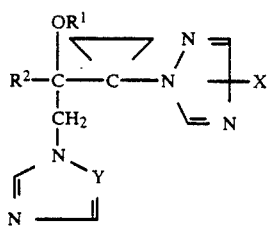

in which
R¹ represents hydrogen, R² represents phenyl which is unsubstituted or substituted by one or two substituents selected from fluorine, chlorine, methyl and phenyl,
X represents chlorine, and
Y represents a nitrogen atom, or
an effective addition product thereof with an acid or metal salt.

2. The method according to claim 1, wherein the substituted bis-azolyl derivative is 1-(4-chlorophenyl)-1-[1-(3-chloro-1,2,4-triazol-1-yl)-cyclopropyl]-2-(1,2,4-triazol-1-yl)-ethan-1-ol of the formula

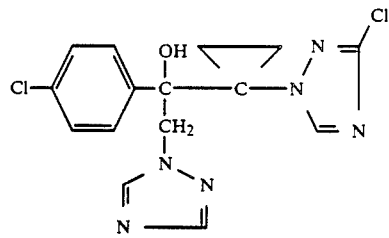

or an effective addition product thereof with an acid or metal salt.

3. The method according to claim 1, wherein the substituted bis-azolyl derivative is 1-[1-(3-chloro-1,2,4-triazol-1-yl)cyclopropyl]-1-phenyl-2-(1,2,4-triazol-1-yl)-ethan-1-ol of the formula

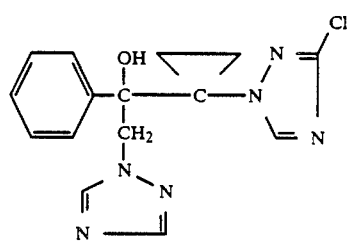

or an effective addition product thereof with an acid or metal salt.

4. The method according to claim 1, wherein the substituted bis-azolyl derivative is 1-[1-(3-chloro-1,2,4-triazol-1-yl)-cyclopropyl]-1-(4-fluorophenyl)-2-(1,2,4-triazol-1-yl)-ethan-1-ol of the formula

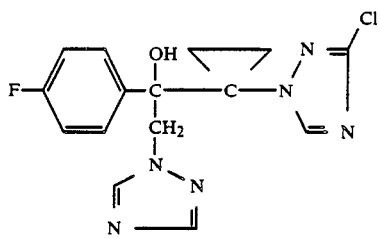

or an effective addition product thereof with an acid or metal salt.

5. The method according to claim 1, wherein the substituted bis-azolyl derivative is 1-[1-(3-chloro-1,2,4-triazol-1-yl)-cyclopropyl]-1-(4-methylphenyl)-2-(1,2,4-triazol-1-yl)-ethan-1-ol of the formula

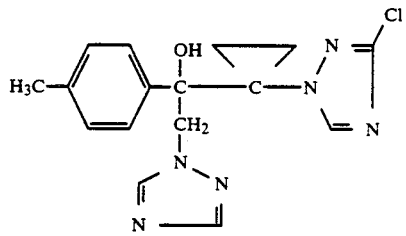

or an effective addition product thereof with an acid or metal salt.

6. The method according to claim 1, wherein the substituted bis-azolyl derivative is 1-(4-biphenyl)-1-[1-(3-chloro-1,2,4-triazol-1-yl)-cyclopropyl]-2-(1,2,4-triazol-1-yl)-ethan-1-ol of the formula

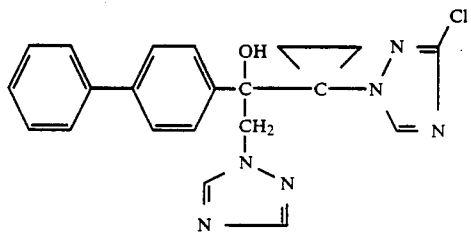

or an effective addition product thereof with an acid or metal salt.

7. The method according to claim 1, wherein the substituted bis-azolyl derivative is applied to a field in which plants are growing or are to be grown.

* * * * *